United States Patent [19]

Kratzer

[11] Patent Number: 4,780,418

[45] Date of Patent: Oct. 25, 1988

[54] METHOD AND APPARATUS FOR MEASURING THE AGGREGATION OF BLOOD PLATELETS OR THE COAGULATION OF BLOOD

[76] Inventor: Michael Kratzer, Leopoldstrasse 56, D-8000, Munich 40, Fed. Rep. of Germany

[21] Appl. No.: 932,422

[22] Filed: Nov. 19, 1986

[30] Foreign Application Priority Data

Nov. 19, 1985 [DE] Fed. Rep. of Germany ....... 3541057

[51] Int. Cl.$^4$ .......................... G01N 33/86; G01N 7/00
[52] U.S. Cl. ........................................ 436/69; 73/64.1; 128/673; 422/73
[58] Field of Search ............................ 422/73; 436/69; 73/64.1; 128/673

[56] References Cited

U.S. PATENT DOCUMENTS 3,911,728 10/1975 Fixot ..................................... 73/64.1
4,201,222 5/1980 Haase .................................. 128/673

FOREIGN PATENT DOCUMENTS 0137761 8/1983 Japan ..................................... 422/73

*Primary Examiner*—Barry S. Richman
*Assistant Examiner*—Robert J. Hill, Jr.
*Attorney, Agent, or Firm*—Anthony A. O'Brien

[57] ABSTRACT

A method and apparatus are disclosed for measuring the aggregation of blood platelets or the coagulation of blood, the apparatus including a capillary tube for drawing blood, a piston in communication with the capillary tube and connected to a motor means for linear displacement thereof, a pressure sensor in the space located between the drawn blood and piston, and a computing means or microprocessing means for comparing the sensed pressure from the pressure sensor with a predetermined value, and providing a measured regulating output to the motor means. The method for measuring the aggregation of blood platelets and coagulation of blood includes the steps of drawing blood into the capillary tube of the moveable piston until the desired pressure is achieved within the capillary tube, and allowing the computing means to then maintain by adjustment of the piston position the pressure within the capillary tube. The computing means is able to determine the amount of blood flowing into the capillary tube during constant pressure regulation, and hence the amount of aggregate of blood platelets and blood coagulation due to a known relationship relating movement of the piston to blood drawn into the cylinder.

13 Claims, 1 Drawing Sheet

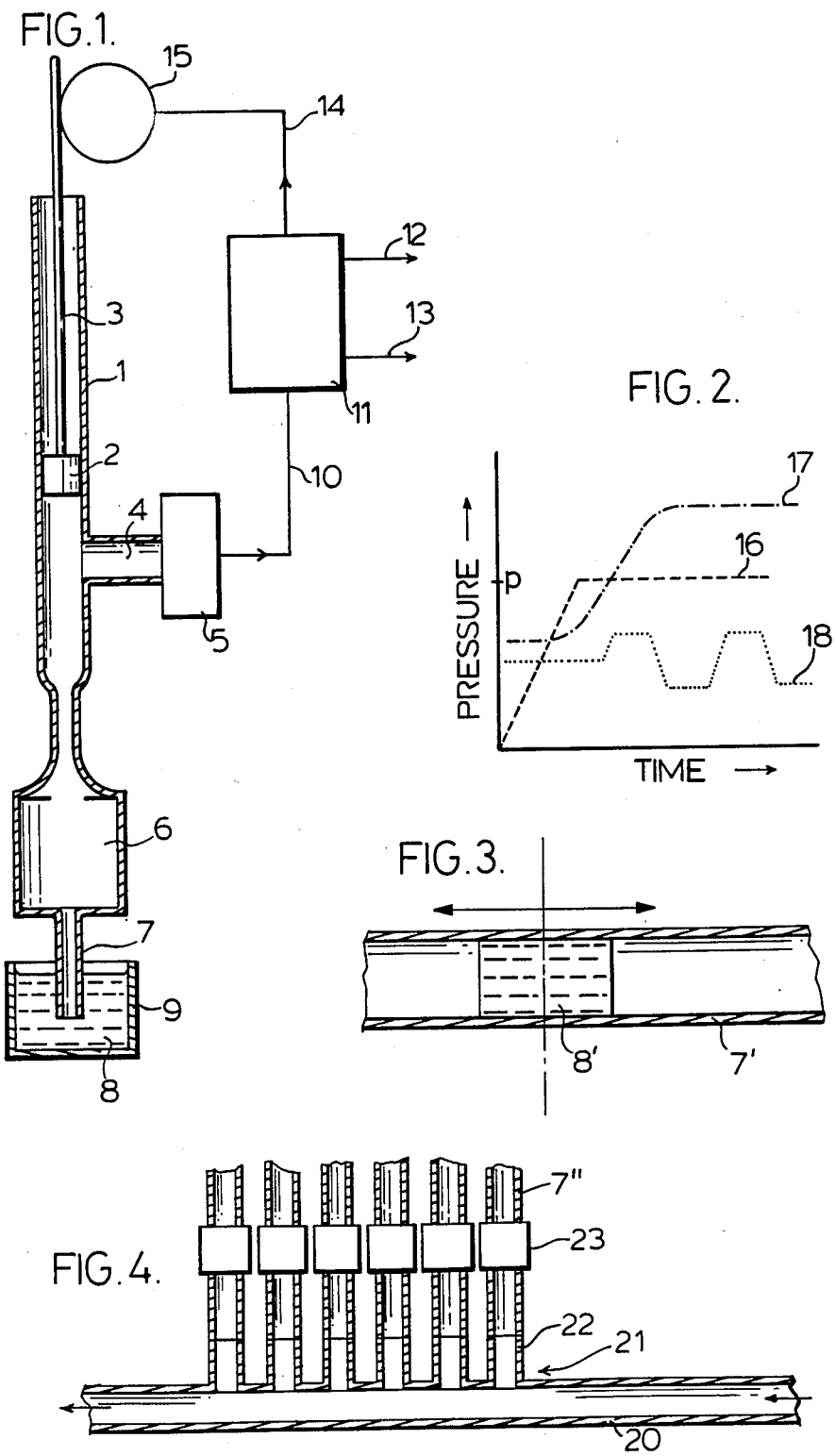

METHOD AND APPARATUS FOR MEASURING THE AGGREGATION OF BLOOD PLATELETS OR THE COAGULATION OF BLOOD

The invention relates to a method for measuring the aggregation of blood-platelets or the coagulation of blood and to an apparatus for the implementation of this method.

BACKGROUND OF THE INVENTION

A method for measuring the coagulation of blood is known from German OS No. 24 06 484, wherein blood is adapted to be drawn from a storage vessel into a tube connected to a cylinder by means of a piston which is provided in the said cylinder and is moved therein in such a manner as to produce suction in the said tube. The piston is connected to a drive which then moves it back and forth in such a manner that the volume of blood drawn into the tube also carries out reciprocating movements in the tube. During these movements, the gas between the piston and the volume of blood is successively expanded and compressed. The change in the pressure of this gas is measured as an indication of the change in viscosity and coagulation of the blood.

With a method of this kind, one problem is that blood-coagulation cannot be measured under physiological conditions since the formation of a thrombus in the tube is influenced by the pressures acting upon it. In addition to this, the change in pressure arising in the gas, which is used in this method to measure coagulation, can be measured only relatively inaccurately and with difficulty. The pressure-measuring unit used in this connection, which consists of a U-shaped glass tube one end of which communicates with the gas-space between the piston and the volume of blood drawn in, is difficult to handle, since care must at all times be taken to ensure that the liquid in the U-shaped glass tube, for example mercury, does not escape therefrom, which might well happen if, as a result of inexpert manipulation, for example, the whole measuring unit were to be turned upside down. This may often happen during shipping and the mercury cannot therefore be placed in the apparatus by the manufacturer. This must be done when it has been set up at its destination, for example in a laboratory. The read-off from the scale fitted to the U-shaped glass tube is relatively time-consuming and inaccurate.

It is therefore the purpose of the present invention to provide a relatively accurate method for measuring the aggregation of blood-platelets or the coagulation of blood, which will allow the measurements to be made under physiological conditions, and an apparatus for the implementation of this method which is relatively simple to handle.

A more important advantage of the invention is that, for the first time, the aggregation of blood-platelets or the coagulation of blood can be measured under physiological conditions, i.e., with the blood under a predetermined, constant pressure. This makes it possible to imitate exactly the procedures taking place in the body, for example as a result of hemorrhage from a cut, or the like.

Another advantage of the invention is that more accurate, reproducible measurements can be taken.

It is also an advantage that the invention makes it possible to simulate cases in which the pressure acting upon the blood can be varied, over a predetermined period of time, in an accurately predetermined manner; for example, the pressure may increase and then decrease according to a predetermined, time-dependent function. Such pressure patterns (blood-pressure fluctuations) may also occur in the human body. It is thus possible, for the first time, to simulate specific disease symptoms by intentional, time-dependent changes in pressure.

Another advantage of the invention is that the design of the apparatus may be extremely functional, reliable, compact and simple.

The method and apparatus according to the invention are highly suitable for carrying out "on-line" measurements on patients who are in a critical phase, for example, after a kidney transplant or the like. At intervals of about 10 minutes, computer-controlled measurements may be carried out automatically. This makes it possible to determine the rate of change in platelet-aggregation and blood coagulation, this being an indication of morbid events, for example consumption-coagulopathy.

BRIEF DESCRIPTION OF THE DRAWINGS

The invention, and configurations thereof, are explained hereinafter in greater detail in conjunction with the drawing attached hereto, wherein:

FIG. 1 illustrates the design of an apparatus according to the invention for measuring blood aggregation or coagulation;

FIG. 2 shows typical pressure-patterns;

FIG. 3 shows another development of the invention; and

FIG. 4 shows another development of the invention for carrying out "on-line" measurements.

DESCRIPTION OF THE PREFERRED EMBODIMENTS

In FIG. 1, blood 8, the blood-platelet aggretation or coagulation of which is to be measured, is located in a beaker or vessel 9. Projecting into this vessel is a capillary tube 7 which preferably communicates with a reservoir 6 for taking blood. This reservoir is connected to a cylinder 1, preferably in the form of a glass tube or the like. Piston 2 is arranged in cylinder 1 in such a manner that it may be moved in the axial direction thereof. The said piston is preferably connected to a piston-rod 3 which is engaged by a drive-element 15, located externally of cylinder 1, which causes piston 2 to move axially. The drive-element is preferably a stepping motor comprising a pinion (not shown) which engages with an area (not shown) of the said piston-rod which is in the form of a toothed rack. The space between piston 2 and capillary tube 7 communicates, through a branch-line 4, with a pressure-sensor 5 by means of which the the pressure in the space can be measured. Pressure-sensor 5 produces an output signal which is proportional to the measured pressure and is fed, through a lead 10, to a computer, microprocessor, or the like 11. As a function of a desired pressure-value fed to it, the microprocessor can produce, in output lead 14, a control-signal which is fed to drive 15. Pressure-sensor 5, lead 10, microprocessor 11, output lead 14 and drive 15 constitute a negative feedback by means of which the pressure in the space between piston 2 and the blood entering capillary tube 7 is held to a predetermined value. This procedure is explained hereinafter in greater detail, it being assumed initially that the pressure is held at a constant desired pressure-value p.

When capillary tube 7 is entered into the blood located in vessel 9 and piston 2 is moved upwardly by drive 15 in FIG. 1, the pressure-difference in the space between the blood entering capillary tube 7 and piston 2, as measured by pressure-sensor 5, rises until desired pressure-value p, fed into microprocessor 11, is reached. This procedure corresponds, in FIG. 2, to the ascending area of curve 16. After pressure p has been reached, microprocessor 11 begins to regulate the pressure in the said space in such a manner as to hold it constant at the desired pressure-value. This means that the blood moves in the capillary tube 7 under accurately reproducible and physiological conditions since, when blood is extravasated, the blood-pressure also remains substantially constant in the human and animal body. When blood enters the capillary tube 7, the pressure displayed at sensor 5 drops slightly by a value $\Delta p$. However, this difference $\Delta p$ is brought to zero in that microprocessor 11 actuates the stepping motor and drive 15 as a function of the difference $\Delta p$. The movement of piston 2 is therefore a function of the quantity of blood entering the capillary tube 7. Since the diameter of cylinder 1, and the distance travelled by the piston, are known to microprocessor 11, the latter can indicate directly at the outlet 12 the quantity of blood entering the tube 7. The change in the quantity of blood flowing, given in volume/time, is a direct measurement of the aggregation of blood-platelets and blood coagulation. Connected to outlet 12 is a display- or recording unit (not shown) which records the pattern of change in the quantity of blood flowing, for direct or subsequent evaluation. Pressure p for evaluation procedures may be displayed at outlet 13. For example, the signals from outputs 12 and 13 may be recorded by an X-Y plotter in the form of time-dependent curves.

It is of critical importance that the pressure in the space between piston 2 and the incoming blood be held constantly and accurately to a predetermined value. If the pressure is held constant, the blood can flow, as already indicated, under physiological conditions, i.e., at a constant pressure. This means that a thrombus can form unimpededly in capillary tube 7, as would be the case during hemorrhage from a cut. In the previously mentioned prior art, on the other hand, the pressure between the piston and the incoming blood would increase appreciably upon formation of a thrombus, so that the incipient thrombus would normally be "torn out" of the capillary tube region. For this reason, events occurring after this "tearing out" can no longer be measured by the apparatus according to the prior art.

The merit of the present invention is that, for the first time, care is taken to ensure that the pressure, at which the blood is drawn into the capillary tube, is held at a predetermined value, since this is indispensable for the undisturbed or natural formation of a thrombus in the capillary tube.

In order to obtain simulations true to nature of events taking place in the human or animal body (e.g. "stress"), during which the blood-pressure varies as a function of time, the pressure in the space between piston 2 and the incoming blood may also be varied according to an accurately predetermined function, as shown by curves 17 and 18 in FIG. 2. According to curve 17, for example, the pressure is increased, as a function of time, from a first to a second value. According to curve 18, the pressure may also fluctuate between a first and a second value at varying intervals of time.

FIG. 3 illustrates a development of the invention in which blood flowing into capillary tube 7' does not move in one direction but is moved back and forth by a corresponding movement of piston 2. This is accomplished, for example, in that a small quantity of blood drawn in is moved back and forth in capillary tube 7' by piston 2 which is caused to reciprocate by drive 15. Again in this case, however, it is of critical importance that, during movement in each direction, the pressure is controlled, by the negative feedback, to a desired value which is either constant (curve 16, FIG. 2) or follows a very accurately predetermined pressure/time function (curves 17, 18, FIG. 2). In this case it is desirable to draw only a small quantity of blood 8' into capillary tube 7', and this blood then carries out the said reciprocating movements. As a result of the intentional reduction of detrimental pressures, in this case again an incipient thrombus will be prevented from being torn away from the inner wall of capillary tube 7' by unduly high pressures.

In the case of the example of the embodiment shown in FIG. 3, in which only a small quantity of blood is drawn in, reservoir 6 (FIG. 1) may be dispensed with.

The reciprocating movement of piston 2 is preferably produced by piston-rod 3 by reversing the direction of rotation of drive 15, the piston having previously carried out a stroke for the purpose of drawing in the said small quantity of blood 8.

In connection with the type of drive 15 used, it is pointed out that movement of the piston in one or both directions may be advantageously accomplished by means of a stepping motor which may be accurately controlled by a digital control-signal released by microprocessor 11 for the purpose of regulating the pressure. Individual steps of the motor, corresponding to a minimal movement of the piston, may be as fine as desired by suitable selection of the motor. It is also conceivable, however, to control the motor in a similar manner. The coupling between piston-rod 3 and motor 15 may also be effected by means of a friction mechanism or some other suitable mechanism.

FIG. 4 illustrates a further development or application of the invention, by means of which "on-line" investigations may be carried out on critical patients in a simple manner, as is desirable after transplants, for example since, in such cases, changes in blood-platelet aggregation and changes in blood-coagulation, as a function of time, may be highly important. A catheter 20, or the like, coming from the patient, through which blood is continuously taken from, and returned to, the patient, comprises a series of consecutive branches 21 (e.g. T-pieces) which lead, through lines 22 and shut-off valves 23, which may for example be electromechanically actuated to capillary tubes 7" which are connected to a measuring unit. Lines 22 may be in the form of rubber hoses while shut-off valves 23 may be in the form of electromagnetically operated hose-clamps. The said shut-off valves are opened in chronological sequence, e.g., at 15-minute intervals, in such a manner that only a single valve is open at one time for the purpose of releasing blood for measurement. As soon as a valve 23 is opened, the piston movement produced by microprocessor 11 causes blood to flow in capillary tube 7". The measuring procedure corresponds to that explained hereinbefore, the blood being drawn into reservoir 6 (FIG. 1) in one direction.

In using the measuring process of FIG. 3 with the apparatus of FIG. 4, the drawing of a small volume of blood into a capillary tube 7" is preferably followed by venting through corresponding valve 23, in order to make the reciprocating movement in capillary tube 7"

possible. If measurements are carried out at 15-minute intervals, this example of embodiment, comprising six branch lines 22 makes it possible to detect changes in blood-platelet aggregation and blood-coagulation over a period of 1.5 hours. Since used capillary tubes 7″ may be automatically replaced by new capillary tubes, correct control of valves 23 makes it possible to continue the investigation indefinitely. The valves 23 are preferably also controlled by microprocessor 11. It is also conceivable to carry out the above "on-line" measurement with a single capillary tube which is automatically replaced after each measurement.

Capillary tubes 7, 7′, 7″ may be in the form of a simple disposable item made out of a synthetic material, for example, and secured to reservoir 6 (FIG. 1) or directly to cylinder 1 (FIG. 3).

It is highly advantageous to use a conventional syringe for cylinder 1 and piston 2.

The sensitivity of the control-loop formed by elements 5,10,11,14,15,3,2 is determined by the volume of the space between piston 2 and the blood drawn into capillary tubes 7, 7′, 7″ and reservoir 6. This means that the accuracy with which the pressure is controlled may be influenced by the dimensions of this space.

Before the measuring procedure is begun, substances which cause the blood to coagulate under specific conditions may be introduced into vessel 9 from the outside. For example, thromboplastins can be added to measure the exongeous path of coagulation.

For the purpose of measuring blood-platelet aggregation, an agent which aggregates the blood-platelets is added to the blood before the measuring procedure is begun. Agents of this kind are disclosed in German Pat. No. 32 47 815.

To summarize, it is pointed out that it is of critical importance, in connection with the present invention, that, in contrast to all previously known measurements, the pressure is preselected as an independent physical magnitude and that the volumetric rate of flow (volume/time) is measured as a dependent physical magnitude. This objective can be accomplished only with the aid of the feedback-loop which is provided here for the first time and which ensures that the predetermined desired (nominal) pressure-values are maintained with a high degree of accuracy in a single manner. In this connection it should be noted that the pressure-values may be constant or may vary as a function of time in a specially predetermined manner. The elimination of detrimental pressures, by predetermined limiting pressure-values, is a reliable way of ensuring that a thrombus can be formed naturally and cannot be harmfully influenced by the action of pressure, as is the case with known measuring procedures. Another advantage is that an intentional and controlled increase in pressure makes it possible, for the first time, to determine the critical pressure leading to the release (separation, detachment) of a thrombus.

Inasmuch as the present invention is subject to many variations, modifications and changes in details, it is intended that all matter contained in the foregoing description or shown on the accompanying drawing shall be interpreted as illustrative and not in a limiting sense.

I claim:

1. A method for measuring the extent of aggregation of blood-platelets in blood or the extent of coagulation of blood comprising the steps of:

positioning a capillary tube, having first and second ends, adjacent a vessel containing a quantity of blood;

positioning a syringe type arrangement comprising a cylinder and a piston adjacent said capillary tube, said first end of said capillary tube extending into said vessel and being in communication with the blood in the vessel and said second end of said capillary tube communicating with the cylinder of the syringe type arrangement;

operating said piston to draw blood from the vessel into said capillary tube, thereby defining a pressure space between the piston and the blood in the capillary tube;

moving the piston in a desired manner to thereby move the blood in the capillary tube in a desired manner;

measuring the pressure in the pressure space;

controlling the moving of said piston based on the pressure measurements to thereby control the pressure in said pressure space in a predetermined manner; and measuring the flow rate of the blood in the capillary tube as a measure of the extent of aggregation of blood-platelets in the blood in the capillary tube or the extent of coagulation of the blood in the capillary tube.

2. The method according to claim 1 wherein the operating step draws a quantity of blood into the capillary tube and the moving step moves the piston so as to move the quantity of blood in the capillary tube in a back and forth motion.

3. The method according to claim 1 wherein the moving of said piston is controlled so as to maintain the pressure in said pressure space at a constant level.

4. The method according to claim 1 wherein the moving of said piston is controlled by a computer so that the pressure in said pressure space varies with time according to a predetermined function, with time-dependent pressure values for the function being stored in the computer.

5. The method according to claim 1 wherein the vessel comprises a catheter through which blood from a patient continuously flows.

6. The method according to claim 1 wherein specific substances which influence the aggregation of blood-platelets in blood or the coagulation of blood are added to the blood in the vessel prior to the operating step.

7. An apparatus for measuring the extent of aggregation of blood-platelets in blood or the extent of coagulation of blood comprising:

a capillary tube having first and second ends;

a cylinder communicating with said first end of the capillary tube;

a piston operatively disposed in the cylinder for drawing blood into the capillary tube through the second end thereof;

a drive for moving said piston;

a pressure sensor disposed between said second end of the capillary tube and the piston for generating pressure signals when blood is contained in the capillary tube to define a pressure space between such blood and the piston, with such pressure signals being indicative of the pressure within such a pressure space; and a computer operatively connected to said pressure sensor and said drive for receiving pressure signals from said pressure sensor, for operating the drive based on received pressure signals from the pressure sensor to control the movement of the piston to thereby control the pressure in a pressure space as defined above in a predetermined manner, and for determining the flow rate of blood in the capillary tube based on movements of the piston.

8. The apparatus according to claim 7 further including a piston-rod connected to the piston and wherein the drive comprises a stepping motor which actuates the piston-rod.

9. The apparatus according to claim 7 wherein the cylinder and the piston are parts of a syringe.

10. The apparatus according to claim 7 further including a blood reservoir connected between the first end of the capillary tube and the cylinder.

11. The apparatus according to claim 7 further including a catheter through which blood from a patient flows and wherein the capillary tube is connected to the catheter through a valve means.

12. The apparatus according to claim 7 wherein the capillary tube is replaceable.

13. The apparatus according to claim 7 wherein the computer also includes a table containing pressure values for calculating a signal for operating the drive.

* * * * *